US011110060B2

(12) United States Patent
Mansour et al.

(10) Patent No.: US 11,110,060 B2
(45) Date of Patent: Sep. 7, 2021

(54) COMPOSITIONS AND METHODS FOR DELIVERING PHARMACEUTICAL AGENTS

(71) Applicant: Arizona Board of Regents on Behalf of the University of Arizona, Tucson, AZ (US)

(72) Inventors: Heidi M. Mansour, Tucson, AZ (US); Rick G. Schnellmann, Tucson, AZ (US); Maria F. Acosta, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 16/759,054

(22) PCT Filed: Oct. 25, 2018

(86) PCT No.: PCT/US2018/057547
§ 371 (c)(1),
(2) Date: Apr. 24, 2020

(87) PCT Pub. No.: WO2019/084290
PCT Pub. Date: May 2, 2019

(65) Prior Publication Data
US 2020/0306190 A1    Oct. 1, 2020

Related U.S. Application Data

(60) Provisional application No. 62/576,953, filed on Oct. 25, 2017.

(51) Int. Cl.
*A61K 9/16* (2006.01)
*A61K 31/185* (2006.01)
*A61K 45/06* (2006.01)

(52) U.S. Cl.
CPC .......... *A61K 9/1623* (2013.01); *A61K 9/1694* (2013.01); *A61K 31/185* (2013.01); *A61K 45/06* (2013.01)

(58) Field of Classification Search
CPC .. A61K 9/1623; A61K 9/1694; A61K 31/185; A61K 45/06
See application file for complete search history.

(56) References Cited

U.S. PATENT DOCUMENTS

| | | |
|---|---|---|
| 5,705,187 A | 1/1998 | Unger |
| 2005/0282893 A1 | 12/2005 | Au et al. |
| 2008/0107741 A1* | 5/2008 | Merisko-Liversidge ............... A61P 35/04 424/489 |
| 2011/0070294 A1* | 3/2011 | Javeri ................. A61K 9/0019 424/450 |
| 2013/0303502 A1 | 11/2013 | Cavanagh et al. |
| 2014/0086983 A1* | 3/2014 | Javeri ...................... A61P 7/06 424/450 |
| 2019/0175505 A1* | 6/2019 | Yang .................... A61K 9/1273 |

OTHER PUBLICATIONS

Korrapati, et al., Suramin: A Potential Therapy for Diabetic Nephropathy, PLoS One Sep. 9, 2013, 8(9):e73655.
Korrapati, et al., Diabetes-Induced Renal Injury in Rats Is Attenuated by Suramin, J. Pharmacol. Exp. Ther. Oct. 2012; 343(1):34-43.
Dupre, et al., Suramin protects from cisplatin-induced acute kidney injury, Am. J. Physiol. Renal Physiol. Feb. 1, 2016; 310(3):F248-58.
Jain et al., Spray Drying in Pharmaceutical Industry: A Review, Research J. Pharma. Dosage Forms and Tech. 2011; 4(2): 74-79.
Mansour, H.M., et al., Nanomedicine in pulmonary delivery, International Journal of Nanomedicine: Dec. 4, 2009: 299-319.
Meenach, S.A., et al., Design, physicochemical characterization, and optimization of organic solution advanced . . . International Journal of Nanomedicine (2013) 8:275-293.
Meenach, S.A., et al., Characterization and aerosol dispersion performance of advanced spray-dried chemotherapeutic PEGylated phospholipid particles for dry powder inhalation delivery in lung cancer., European Journal of Pharmaceutical Sciences (2013) 49 (4): 699-711.
International Search Report & Written Opinion, International Patent Application No. PCT/US2018/057547, dated Jan. 17, 2019, 13 pages.

* cited by examiner

*Primary Examiner* — Robert A Wax
*Assistant Examiner* — Olga V. Tcherkasskaya
(74) *Attorney, Agent, or Firm* — Casimir Jones, S.C.; Tanya A. Arenson

(57) ABSTRACT

Provided herein are compositions and methods for wound healing. In particular, provided herein are spray dried suramin for use in wound healing and other applications.

15 Claims, 16 Drawing Sheets

XRPD

ATR-FTIR

XRPD

ATR-FTIR

- Characteristic identifying atoms that are unique to suramin are Na and S

| Element | Element Wt.% | Wt.% Error |
|---|---|---|
| C | 31.86 | ± 0.30 |
| O | 28.39 | ± 0.30 |
| Na | 10.87 | ± 0.08 |
| S | 17.85 | ± 0.09 |
| Pt | 11.03 | ± 0.30 |
| Total | 100.00 | |

XRPD

ATR-FTIR

COMPOSITIONS AND METHODS FOR DELIVERING PHARMACEUTICAL AGENTS

CROSS REFERENCE TO RELATED APPLICATIONS

This application is a U.S. 371 national phase entry of International Patent Application No. PCT/US2018/057547, filed Oct. 25, 2018, which claims priority to and the benefit of U.S. Provisional Application No. 62/576,953, filed Oct. 25, 2017, which are hereby incorporated by reference in their entireties.

FIELD

Provided herein are compositions and methods for wound healing. In particular, provided herein are spray dried suramin for use in wound healing and other applications.

BACKGROUND

A chronic wound is a wound that does not heal in an orderly set of stages and in a predictable amount of time the way most wounds do; wounds that do not heal within three months are often considered chronic. Chronic wounds are detained in one or more of the phases of wound healing. For example, chronic wounds often remain in the inflammatory stage for too long. To overcome that stage and jump-start the healing process a number of factors need to be addressed such as bacterial burden, necrotic tissue, and moisture balance of the whole wound. In acute wounds, there is a precise balance between production and degradation of molecules such as collagen; in chronic wounds this balance is lost and degradation plays too large a role.

Chronic wounds may never heal or may take years to do so. These wounds cause patients severe emotional and physical stress and create a significant financial burden on patients and the whole healthcare system. In addition to poor circulation, neuropathy, and difficulty moving, factors that contribute to chronic wounds include systemic illnesses, age, and repeated trauma. Comorbid ailments that may contribute to the formation of chronic wounds include vasculitis (an inflammation of blood vessels), immune suppression, pyoderma gangrenosum, diabetes, cancer treatments, and diseases that cause ischemia. Immune suppression can be caused by illnesses or medical drugs used over a long period, for example steroids. Emotional stress can also negatively affect the healing of a wound, possibly by raising blood pressure and levels of cortisol, which lowers immunity.

Though treatment of the different chronic wound types varies slightly, appropriate treatment seeks to address the problems at the root of chronic wounds, including ischemia, bacterial load, and imbalance of proteases. Periwound skin issues should be assessed and their abatement included in a proposed treatment plan. Various methods exist to ameliorate these problems, including antibiotic and antibacterial use, debridement, irrigation, vacuum-assisted closure, warming, oxygenation, moist wound healing, removing mechanical stress, and adding cells or other materials to secrete or enhance levels of healing factors.

Additional treatments for wounds are needed.

SUMMARY

There is a long unmet need for new treatments for wounds, in particular chronic wounds, as well as a large patient population. The present invention meets this need by providing improved formulations of suramin for use in wound healing in a variety of patient populations. For example, in some embodiments, provided herein is a composition, comprising: suramin nano or microparticles. In some embodiments, the nano or microparticles further comprise a pharmaceutically acceptable carrier. In some embodiments, the pharmaceutically acceptable carrier is a sugar (e.g., trehalose). In some embodiments, suramin and trehalose are present at a molar ratio of 20:80 to 80:20 suramin:trehalose (e.g., a molar ratio of 50:50 suramin:trehalose). In some embodiments, the pharmaceutically acceptable carrier is a PEGylated phospholipid. In some embodiments, the suramin and said PEGylated phospholipid are present at a molar ratio of 50:50 suramin: PEGylated phospholipid. In some embodiments, the suramin is encapsulated by the PEGylated phospholipid. In some embodiments, the PEGylated phospholipid is a mixture of dipalmitoylphosphatidylcholine (DPPC) and dipalmitoylphosphoethanolamine-poly (ethylene glycol) (DPPE-PEG). In some embodiments, the DPPC and DPPE-PEG are present at a 95:5 ratio. In some embodiments, the PEG has a molecular weight of 2000 to 5000. In some embodiments, the composition is spray dried. In some embodiments, the nano or microparticles are amorphous.

In some embodiments, the nano or microparticles are generated by a method, comprising: a) preparing a first solution comprising said suramin in an organic solvent and a second solution comprising said pharmaceutically acceptable carrier in an organic solvent; and b) co-spraying the first and second solutions using a spray drying apparatus. In some embodiments, the organic solvent is methanol.

Further embodiments provide a method of treating wounds in a subject, comprising: administering the compositions described herein to a subject with a wound under conditions such that said wound heals. In some embodiments, the wound is an acute wound or a chronic wound or ulcer. In some embodiments, the subject has diabetes or mucositis (e.g., induced by cancer treatment such as radiation). In some embodiments, the method further comprises administering an additional treatment for the wound (e.g., an antibiotic or a pain reliever (e.g., non-steroidal anti-inflammatory agent)).

Yet other embodiments provide the use of the compositions described herein to treat or heal a wound in a subject.

Certain embodiments provide the compositions described herein for use in treating a wound.

Additional embodiments are described herein.

DEFINITIONS

Figure 1:
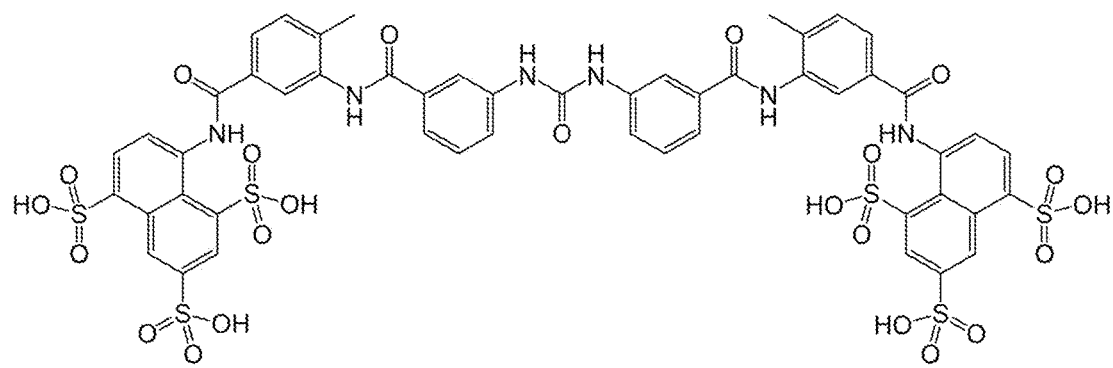
FIG. 1: suramin chemical structure.
Figure 2:
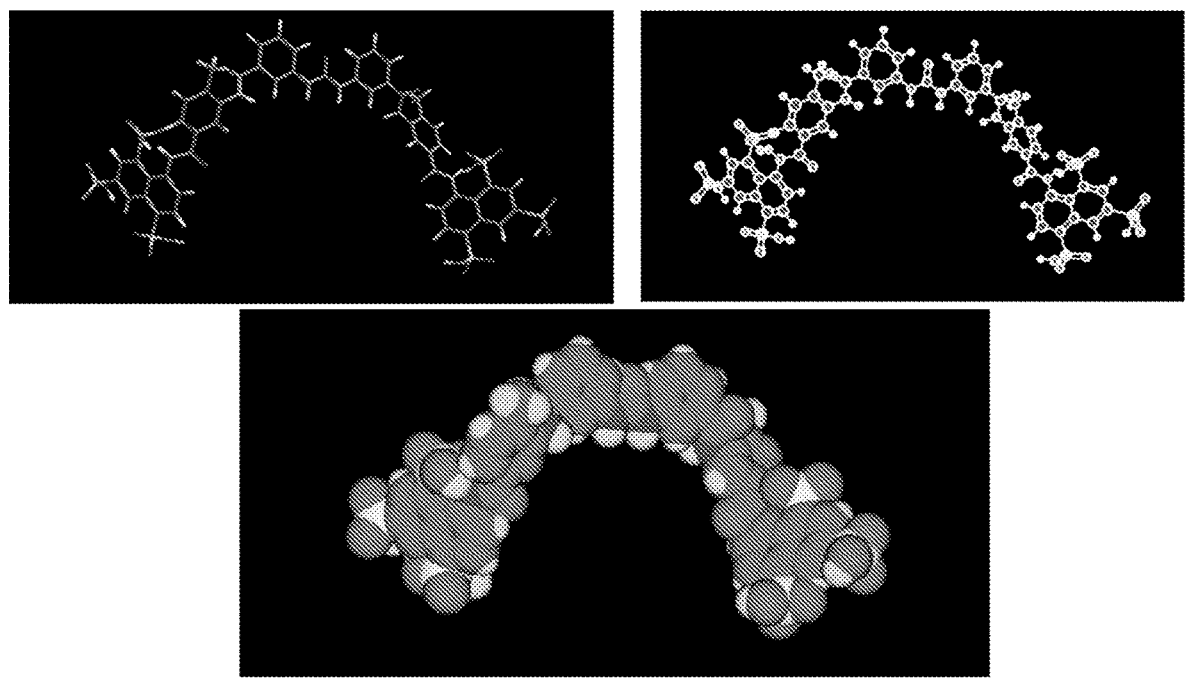
FIG. 2: stick, ball and stick, and space-filled 3-D models of suramin
Figure 3:
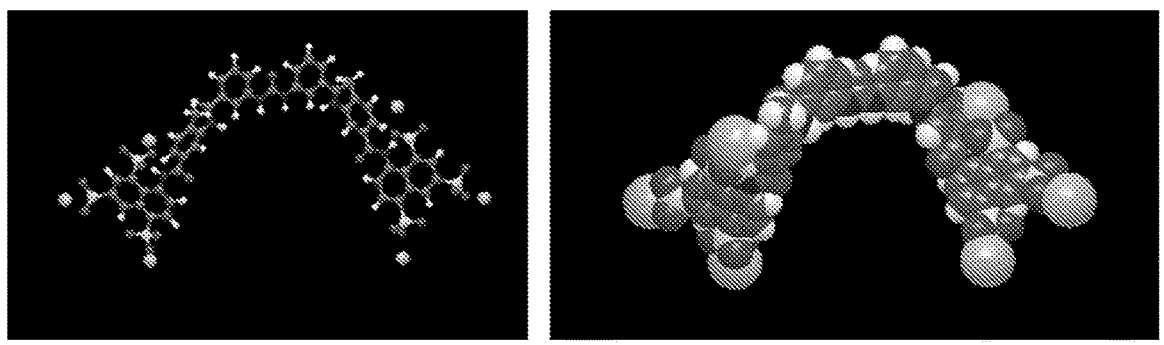
FIG. 3: stick, ball and stick, and space-filled 3-D models of sodium suramin.
Figure 4:
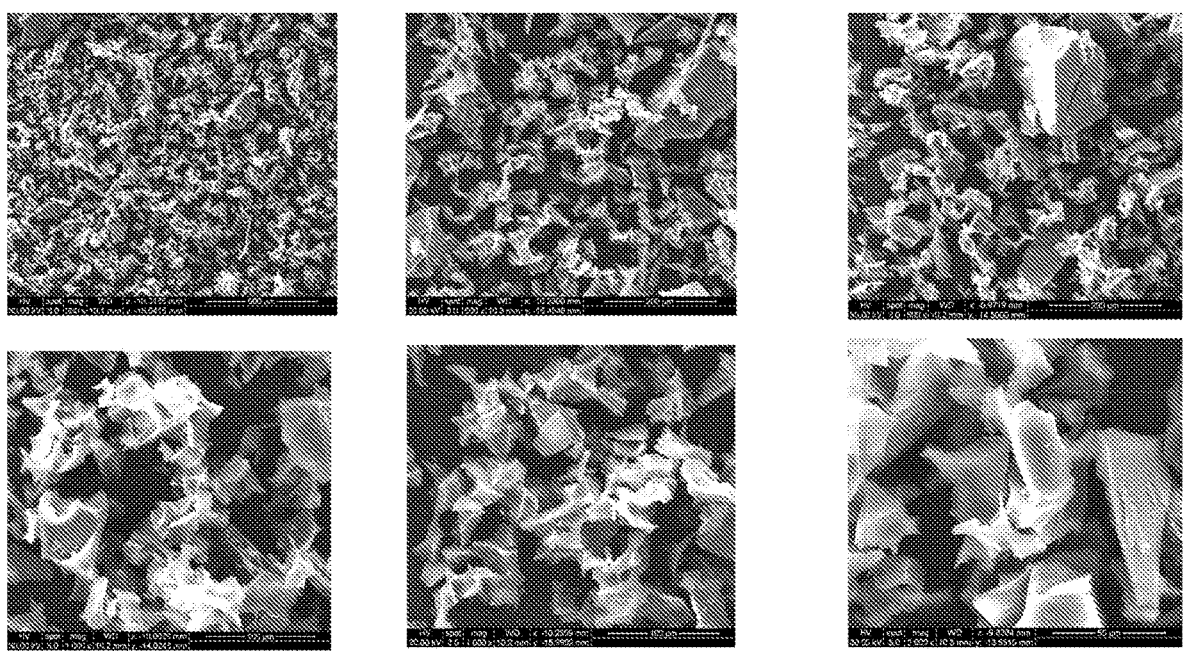
FIG. 4: scanning electron microscopy (SEM) of raw sodium suramin particles.
Figure 5:
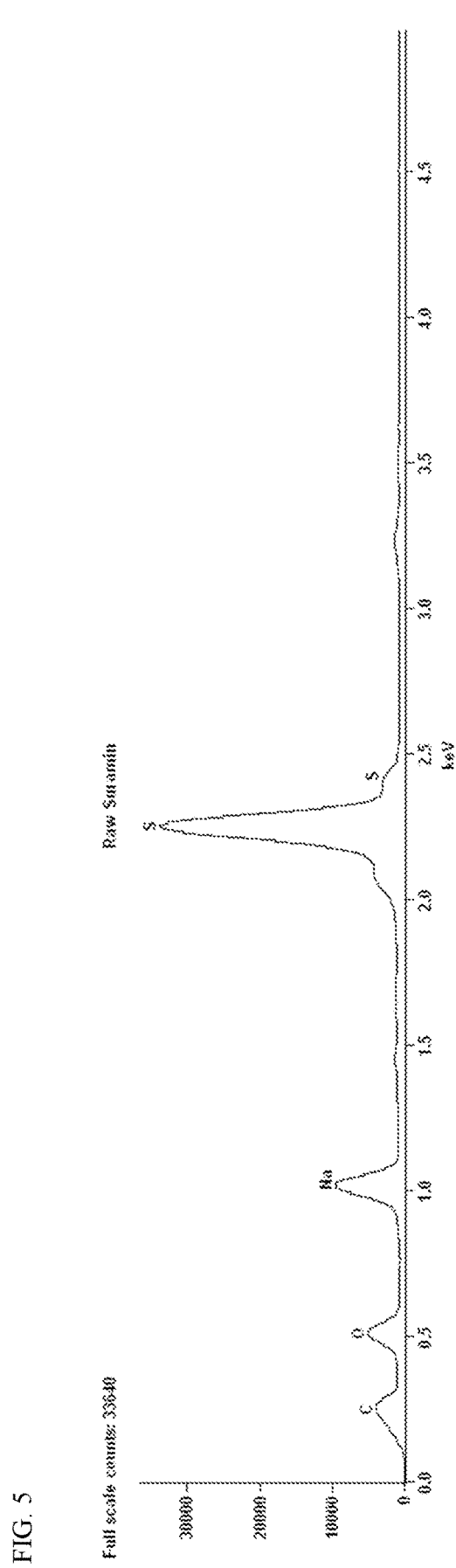
FIG. 5: In situ SEM with simultaneous EDX (Energy Dispersive X-ray) for chemical identification in the solid-state particles: raw sodium suramin.
Figure 6:
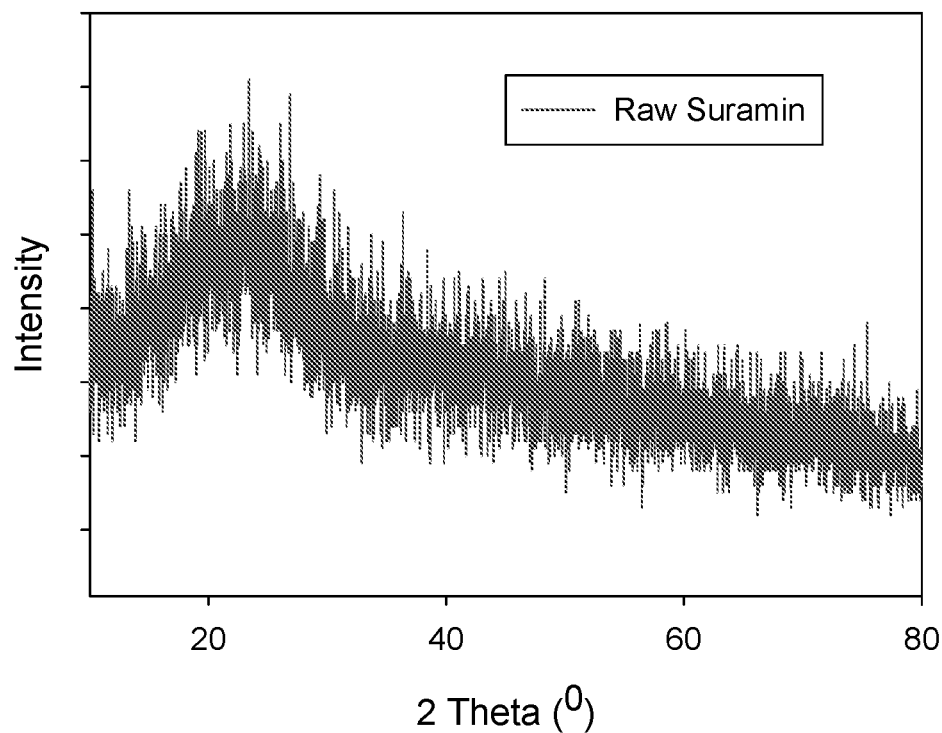
FIG. 6: X-Ray powder diffraction (XRPD) of sodium suramin.
Figure 7:
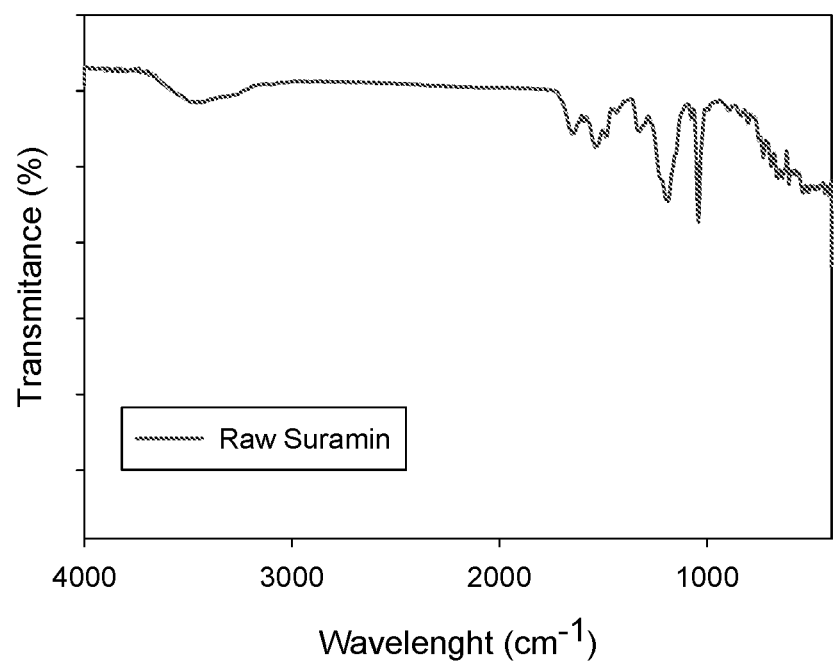
FIG. 7: solid-state spectroscopy: molecular fingerprint of sodium suramin.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human or non-human mammal subject.

As used herein, the term "diagnosed," as used herein, refers to the recognition of a disease by its signs and symptoms (e.g., resistance to conventional therapies), or genetic analysis, pathological analysis, histological analysis, and the like.

As used herein, the term "effective amount" refers to the amount of a compound (e.g., a compound of the present disclosure) sufficient to effect beneficial or desired results. An effective amount can be administered in one or more administrations, applications or dosages and is not limited to a particular formulation or administration route.

As used herein, the term "co-administration" refers to the administration of at least two agent(s) (e.g., a compound of the present disclosure) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa., (1975)).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present disclosure.

As used herein, the terms "purified" or "to purify" refer, to the removal of undesired components from a sample. As used herein, the term "substantially purified" refers to molecules that are at least 60% free, at least 65% free, at least 70% free, at least 75% free, at least 80% free, at least 85% free, at least 90% free, at least 95% free, at least 96% free, at least 97% free, at least 98% free, at least 99% free, or 100% free from other components with which they usually associated.

As used herein, the term "modulate" refers to the activity of a compound (e.g., a compound of the present disclosure) to affect (e.g., to promote or retard) an aspect of cellular function.

As used herein, the phrase "in need thereof" means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, condition, or injury is prevalent.

DETAILED DESCRIPTION

Suramin has a long historical precedence of safety in humans spanning 100 years (see, e.g., Korrapati, et al., PLoS One 2013 Sep. 9, 8(9):e73655; Korrapati, et al., J. Pharmacol. Exp. Ther. 2012 October; 343(1):34-43; Dupre, et al., Am. J. Physiol. Renal Physiol. 2016 Feb. 1; 310(3):F248-58). Currently, for example, it is approved for African Sleeping Sickness in Germany. Provided herein are new spray dried formulations of suramin for use in wound healing (e.g., wound healing in chronic wound injury in mucositis (head/neck cancer therapy-induced) and chronic wound injury in diabetic foot ulcers).

Accordingly, provided herein is suramin nano or microparticles. In some embodiments, the composition comprises amorphous particles.

In some embodiments, suramin is present in a dry powder or other form generated by spray drying (See e.g., below and Jain et al., Research J. Pharma. Dosage Forms and Tech. 2011; 4(2): 74-79). In some embodiments, suramin is spray dried alone or with a pharmaceutically acceptable carrier. In some embodiments, the pharmaceutically acceptable carrier is a sugar (e.g., D-mannitol, lactose, trehalsose or xylitol). In some embodiments, the suramin and trehalose are present at a molar ratio of 20:80 to 80:20 suramin:trehalose (e.g., 50:50).

In some embodiments, the carrier is a lipid or phospholipid (e.g., phosphatidylcholine, cholesterol, phosphatidylethanolamine, phosphatidylglycerol, phosphatidylinositol, phosphatidylserine, sphingomyelin, cardiolipin, dioleoylphosphatidylglycerol (DOPG), diacylphosphatidylcholine, diacylphosphatidylethanolamine, ceramide, sphingomyelin, cephalin, cholesterol, cerebrosides, diacylglycerols, dioleoylphosphatidylcholine (DOPC), dimyristoylphosphatidylcholine (DMPC), and dioleoylphosphatidylserine (DOPS), diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dipalmitoylphosphatidylcholine (DPPC), dipalmitoylphosphatidylglycerol (DPPG), palmitoyloleoylphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkylaryl sulfate polyethyloxylated fatty acid amides, dioctadecyldimethyl ammonium bromide, polyethylene glycol (PEG), or PEG modified lipids). In some embodiments, the PEG is 2000-5000 mw PEG.

Generally, during spray-drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by GEA Group (Niro, Inc.; Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C. The spray dryer outlet temperature will vary depending upon such factors as the feed temperature and the properties of the materials being dried. Generally, the outlet temperature is about 50° C. to about 150° C. The spray dryer outlet temperature will vary depending upon such factors as the feed temperature and the properties of the materials being dried. Generally, the outlet temperature is about 50° C. to about 150° C.

A nitrogen source with a specified moisture level may be flown over, across, or through the dry powder to add a specific moisture content to the dry powder. Such moisture can provide the desired working density of the powder. Spray drying methods in accordance with the invention are described in the Examples herein and in U.S. Pat. Nos. 6,848,197 and 8,197,845, incorporated herein by reference.

If desired, the respirable dry particles that are produced can be fractionated by volumetric size, for example, using a sieve, or fractioned by aerodynamic size, for example, using a cyclone, and/or further separated according to density using techniques known to those of skill in the art.

In some embodiments, the suramin particles are generated by a method, comprising: a) preparing a first solution comprising said suramin in an organic solvent; and b) spraying the first solution using a spray drying apparatus. In some embodiments, the method further comprises the steps of preparing a second solution comprising said pharmaceutically acceptable carrier in an organic solvent; and co-spraying the first and second solutions. In some embodiments, the organic solvent is methanol.

Further embodiments provide a method of promoting wound healing comprising administering the suramin compositions described herein to a subject in need thereof.

In some embodiments, suramin is provided in the form of a dry powder, for example, a powder mix of the compound in a suitable powder base such as lactose, starch, starch derivatives such as hydroxypropylmethyl cellulose and polyvinylpyrrolidone (PVP).

The compounds may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Certain pharmaceutically acceptable salts are listed in Berge, et al., Journal of Pharmaceutical Sciences, 66:1-19 (1977), incorporated herein by reference in its entirety.

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprise a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP branched chain esters may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate. Likewise, those for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Preferred unit dosage formulations are those containing a daily dose or unit, daily subdose, as herein above-recited, or an appropriate fraction thereof, of an agent. It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

In certain embodiments, the present invention provides instructions for administering said wound healing agents (e.g., suramin compositions) to a subject. In certain embodiments, the present invention provides instructions for using the compositions contained in a kit for the treatment of wounds (e.g., providing dosing, route of administration, decision trees for treating physicians for correlating patient-specific characteristics with therapeutic courses of action).

In certain embodiments, the present invention provides instructions for using the compositions contained in the kit to treat a variety of medical conditions associated with wounds.

Various delivery systems are known and can be used to administer therapeutic agents (e.g., wound healing agents (e.g., suramin) described in the present invention) of the present invention, e.g., encapsulation in liposomes, microparticles, microcapsules, receptor-mediated endocytosis, and the like. Methods of delivery include, but are not limited to, intra-arterial, intra-muscular, intravenous, intra-nasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the agents identified can be administered to subjects or individuals having, susceptible to or at risk of developing chronic wounds and correlated conditions. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the agents (e.g., suramin) provided herein are administered at about 0.01 mg/kg to about 200 mg/kg, more preferably at about 0.1 mg/kg to about 100 mg/kg, even more preferably at about 0.5 mg/kg to about 50 mg/kg. When the wound healing agents (e.g., suramin) described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

The present invention also includes methods involving co-administration of the agents (e.g., suramin) described herein with one or more additional active agents. Indeed, it is a further aspect of this invention to provide methods for enhancing prior art therapies and/or pharmaceutical compositions by co-administering an wound healing agents (e.g., suramin) described herein. In co-administration procedures, the agents may be administered concurrently or sequentially. In one embodiment, the agents (e.g., suramin) described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, in some embodiments, the additional agent is an antibiotic, pain reliever (e.g., NSAID) or other wound healing agent.

In certain embodiments, the present invention provides methods (e.g., therapeutic applications) for treating conditions associated with wounds (e.g., chronic or slow to heal wounds).

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXPERIMENTAL

Example 1

This Example describes spray drying of suramin with trehalose in a number of different ratios.

Figure 8:
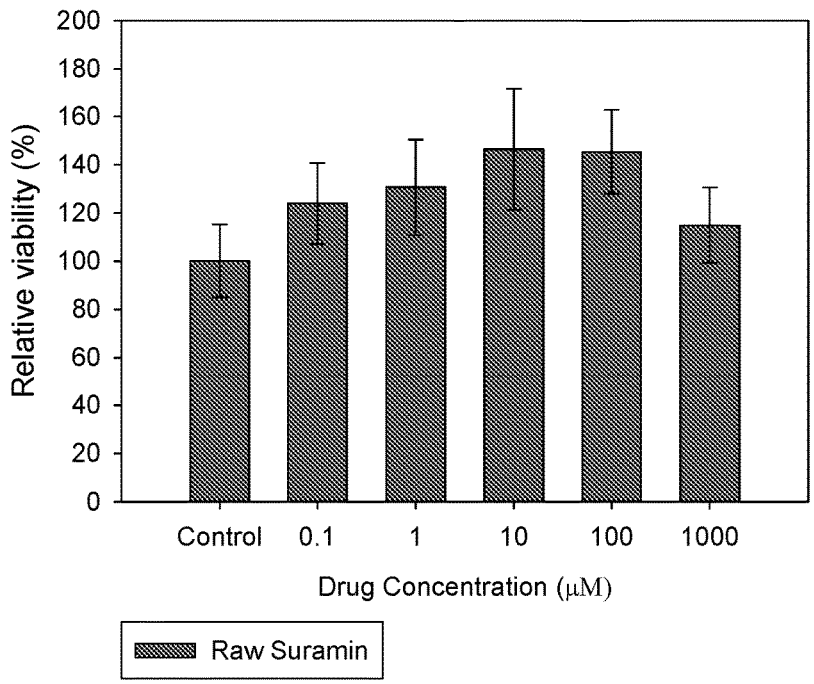
FIG. 8: In vitro viability of human buccal cell line (T146): dose-response of sodium suramin for safety/toxicity.
Figure 9:
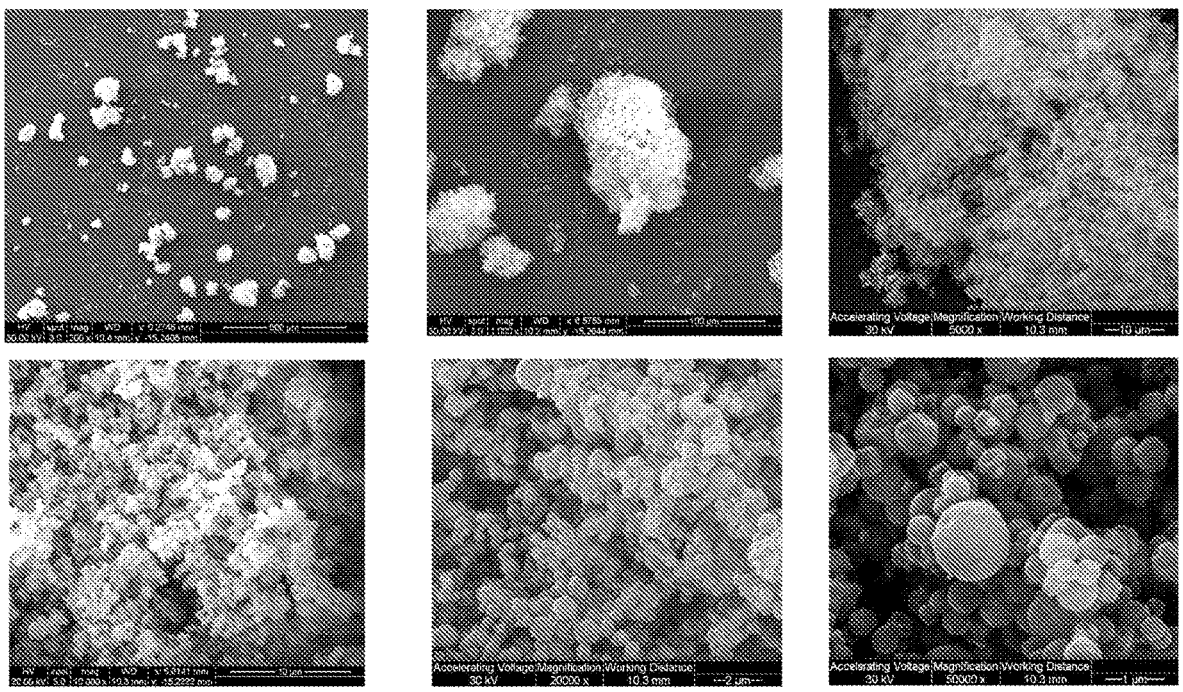
FIG. 9: SEM of spray dried bioengineered suramin nanoparticles & microparticles in the solid-state at different SEM magnification levels (sodium suramin:trehalose 20:80).
Figure 10:
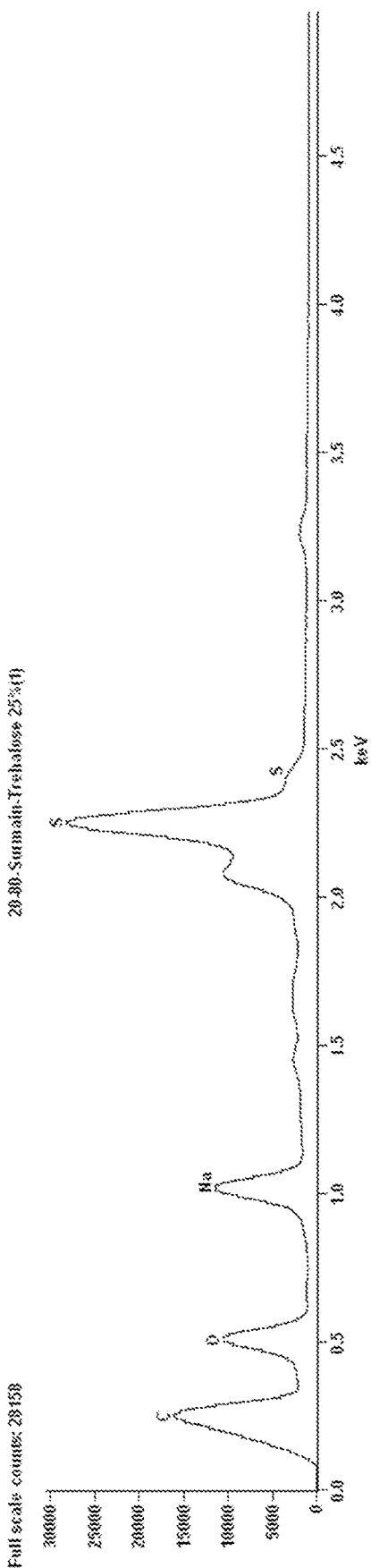
FIG. 10: In situ SEM with simultaneous EDX for chemical identification in the solid-state particles. spray dried bioengineered sodium suramin:trehalose 20:80.
Figure 11:
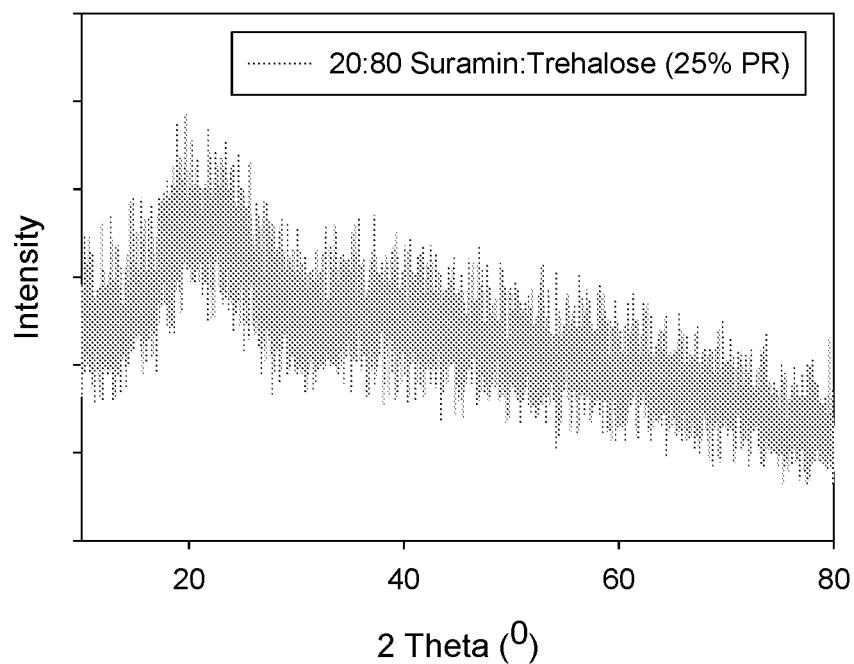
FIG. 11: XRPD of SD nanoparticles and microparticles (sodium suramin:trehalose 20:80).
Figure 12:
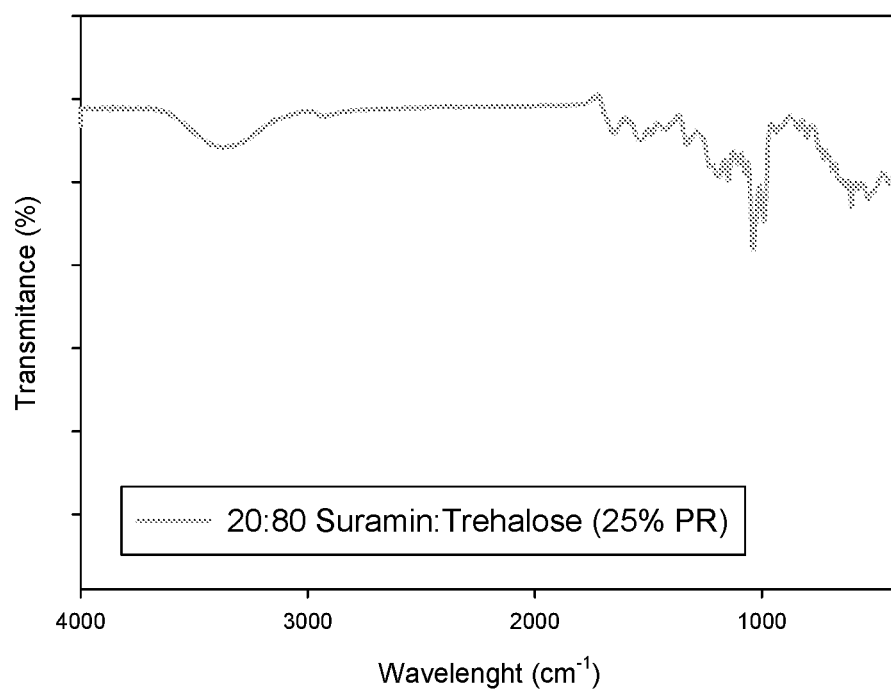
FIG. 12: solid-state spectroscopy: molecular fingerprint (sodium suramin:trehalose 20:80).
Figure 13:
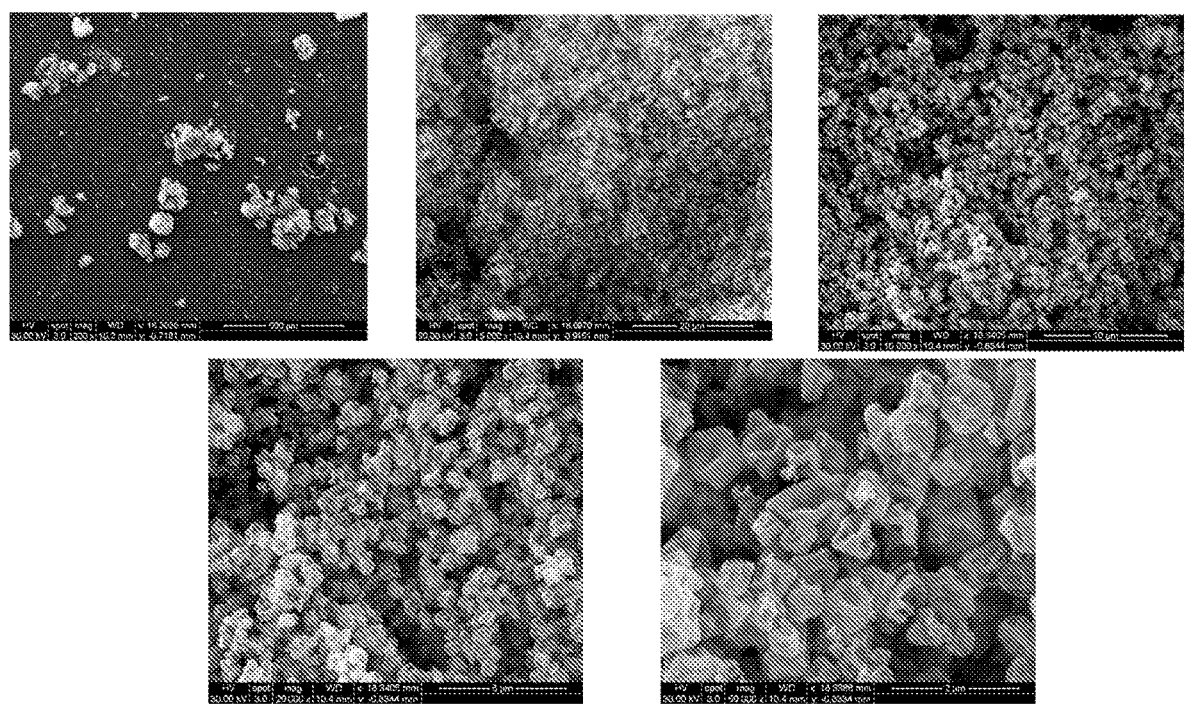
FIG. 13: SEM of spray dried bioengineered suramin nanoparticles & microparticles in the solid-state at different SEM magnification levels (sodium suramin:trehalose 50:50).
Figure 14:
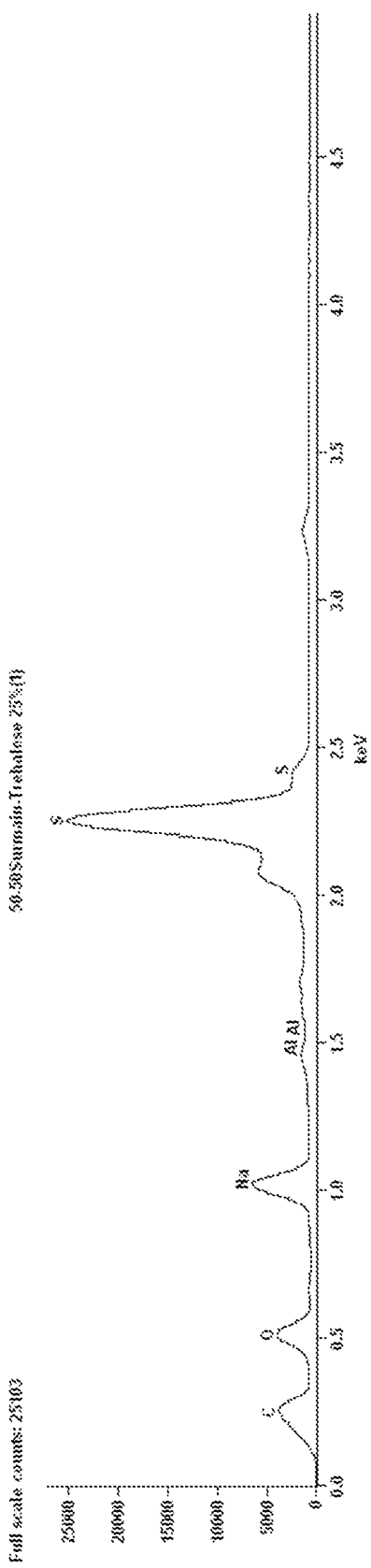
FIG. 14: In situ SEM with simultaneous EDX for chemical identification in the solid-state particles. Spray dried bioengineered sodium suramin:trehalose 50:50.
Figure 15:
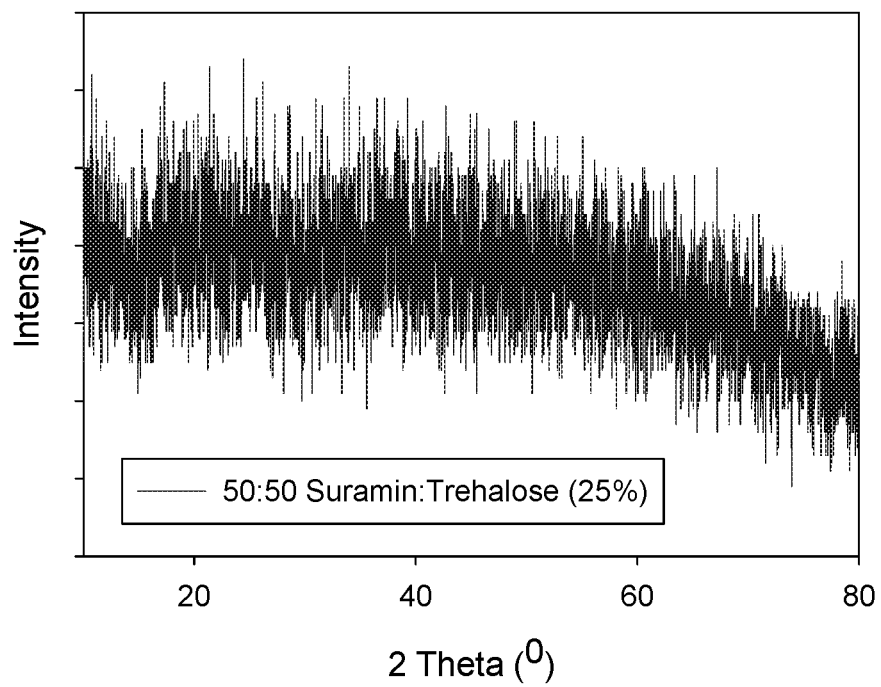
FIG. 15: XRPD of SD nanoparticles and microparticles (sodium suramin:trehalose 50:50).
Figure 16:
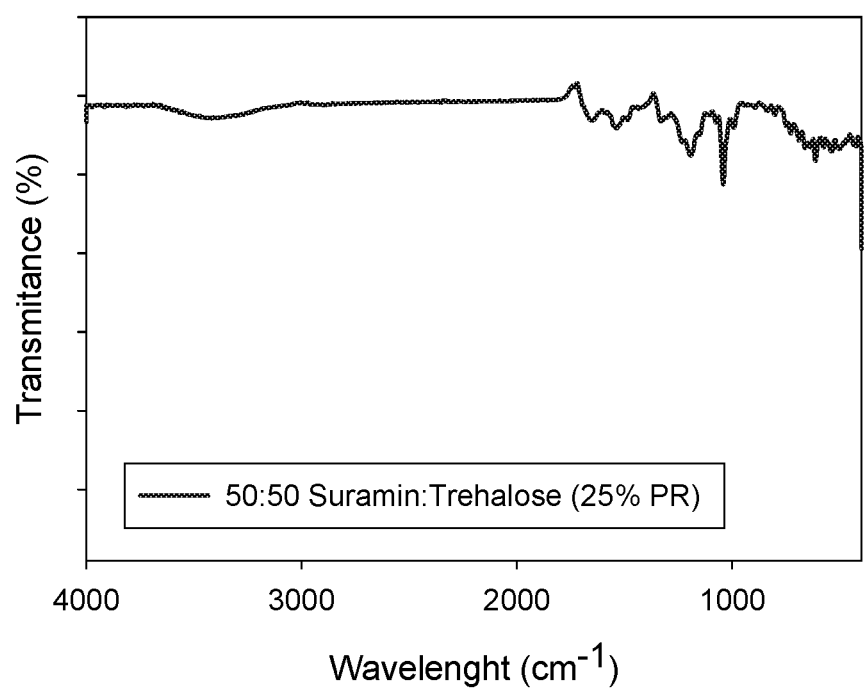
FIG. 16: solid-state spectroscopy: molecular fingerprint (sodium suramin:trehalose 50:50).
Figure 17:
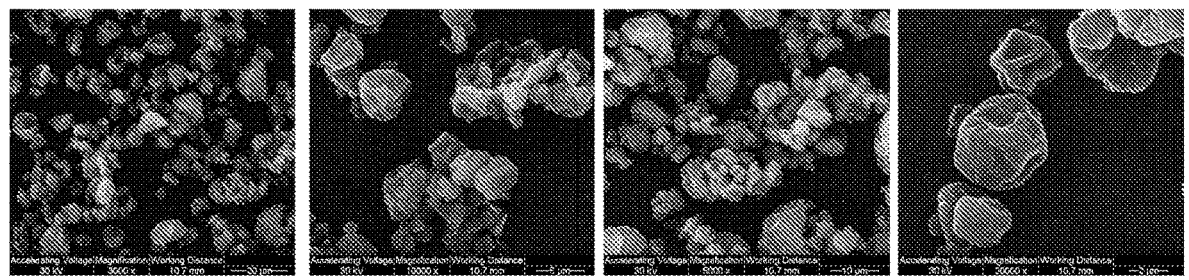
FIG. 17: SEM of spray dried bioengineered suramin nanoparticles & microparticles in the solid-state at different SEM magnification levels (PEGylated phospholipid encapsulated suramin).
Figure 18:
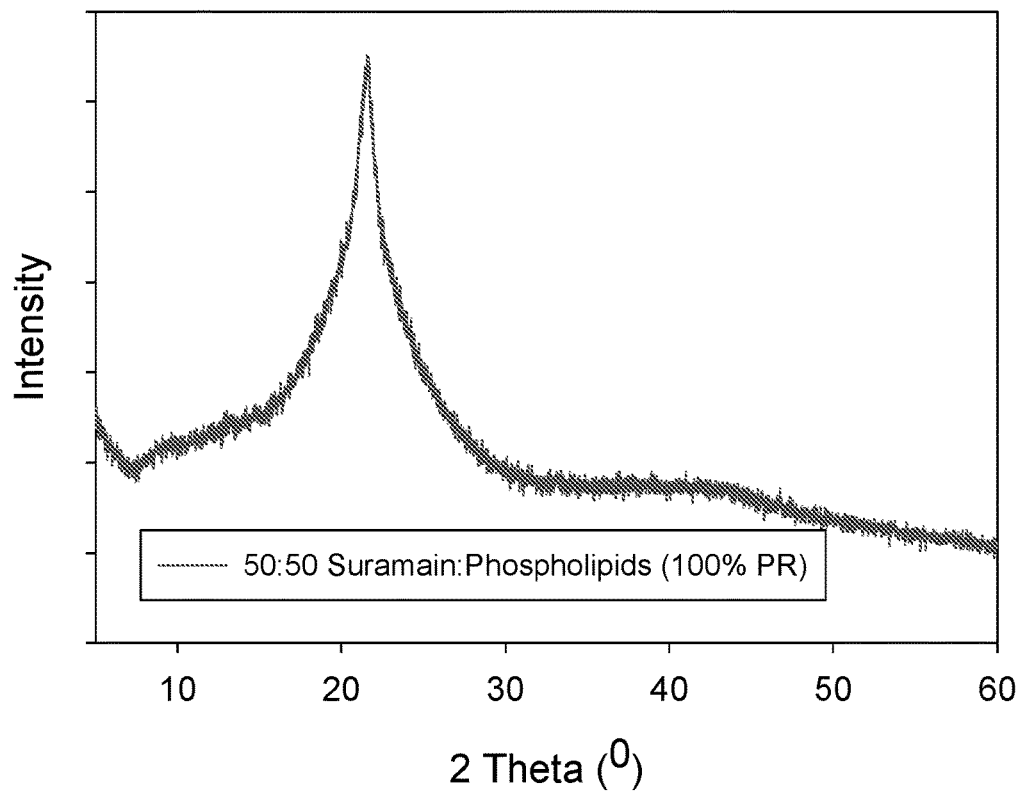
FIG. 18: XRPD of SD nanoparticles and microparticles (PEGylated phospholipid encapsulated suramin).
Figure 19:
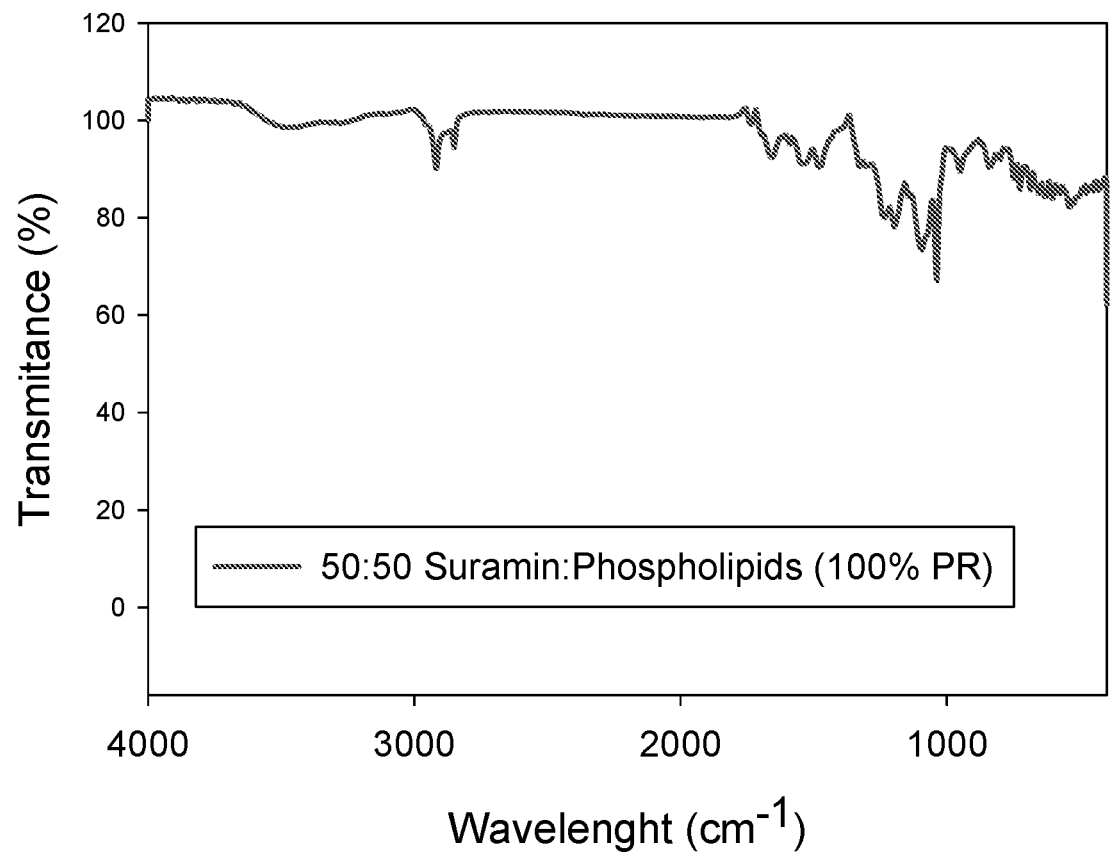
FIG. 19: solid-state spectroscopy: molecular fingerprint (PEGylated phospholipid encapsulated suramin).
Figure 20:
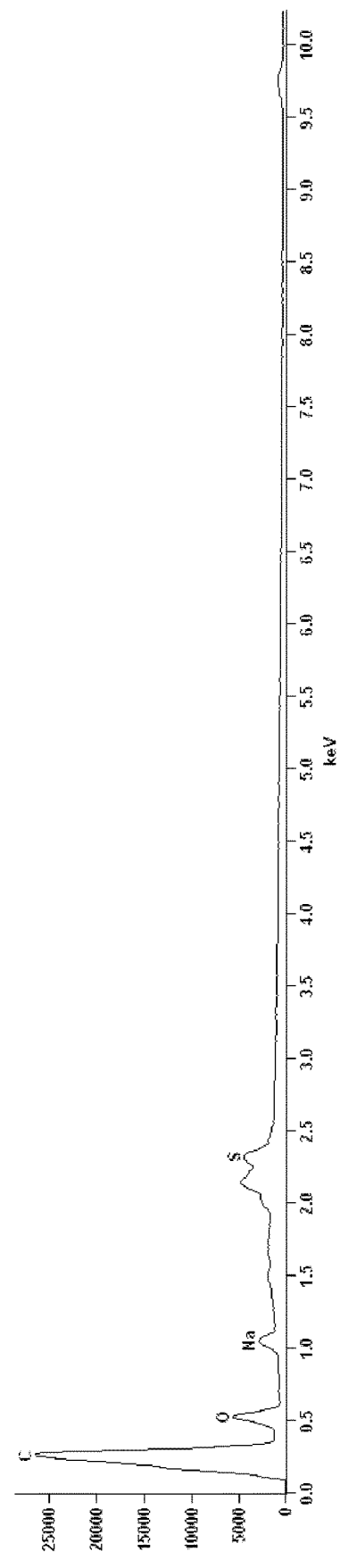
FIG. 20: In situ SEM with simultaneous EDX for chemical identification in the solid-state particles. Spray dried bioengineered PEGylated phospholipid encapsulated suramin.
Figure 21:
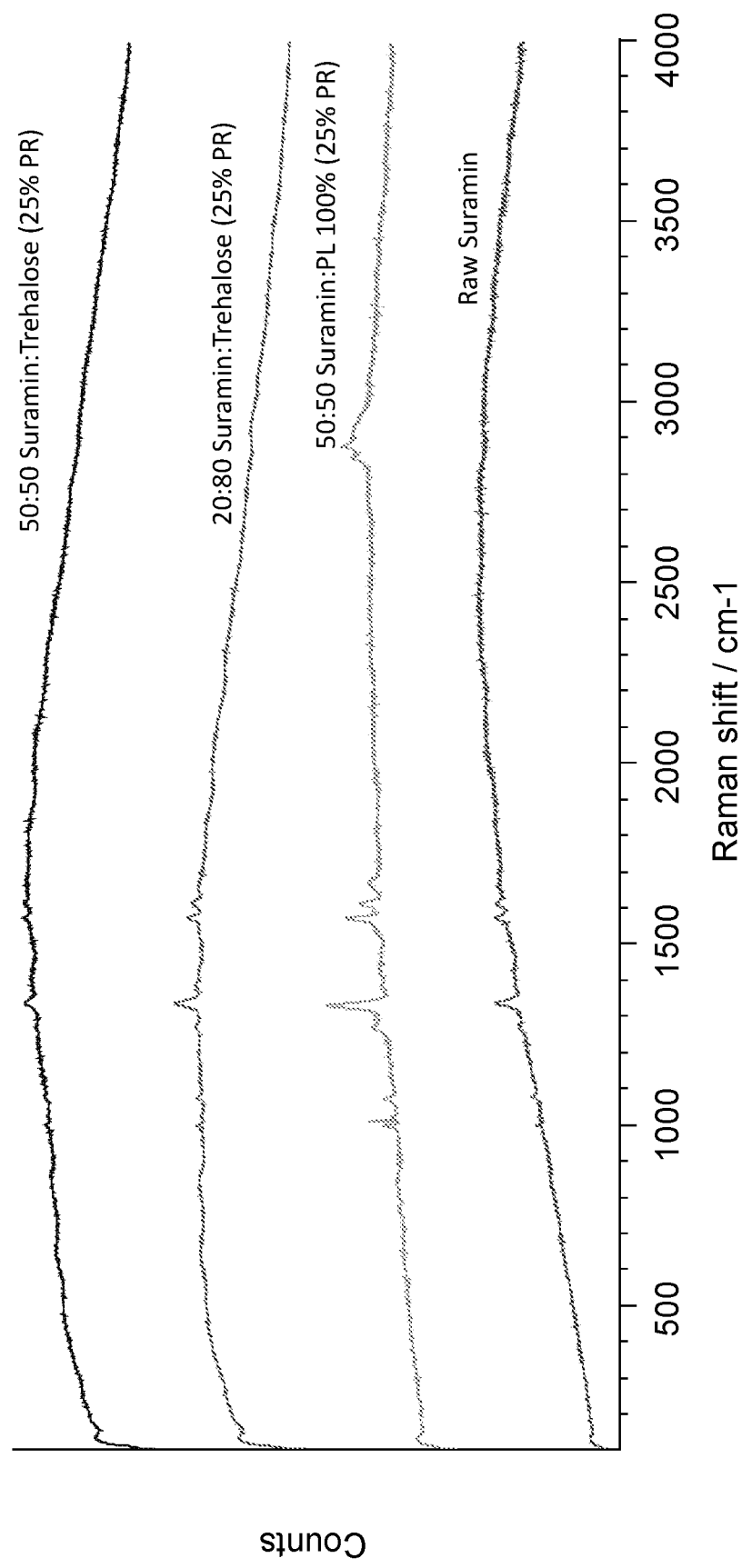
FIG. 21: Raman Spectroscopy: molecular fingerprint spectroscopy that is complementary to ATR-FTIR.
Figure 22:
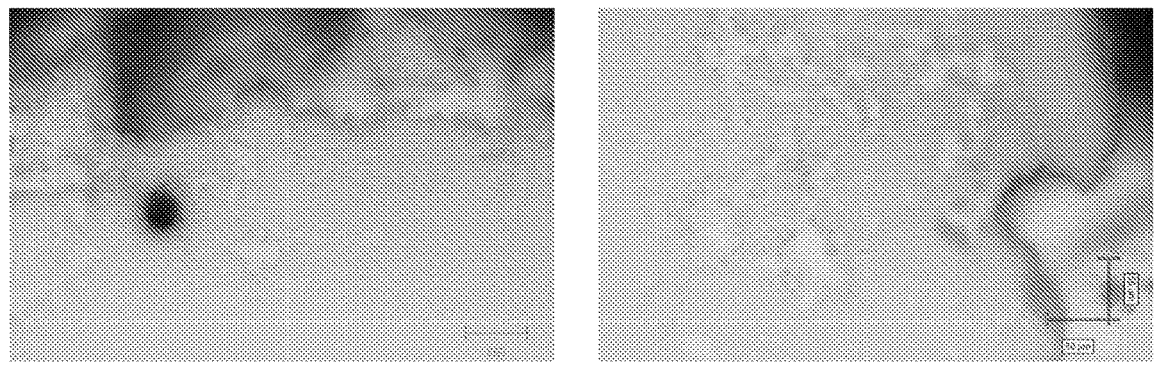
FIG. 22: confocal Raman microspectroscopy: simultaneous confocal laser scanning microscopy+Raman Spectroscopy in situ.
Figure 23:
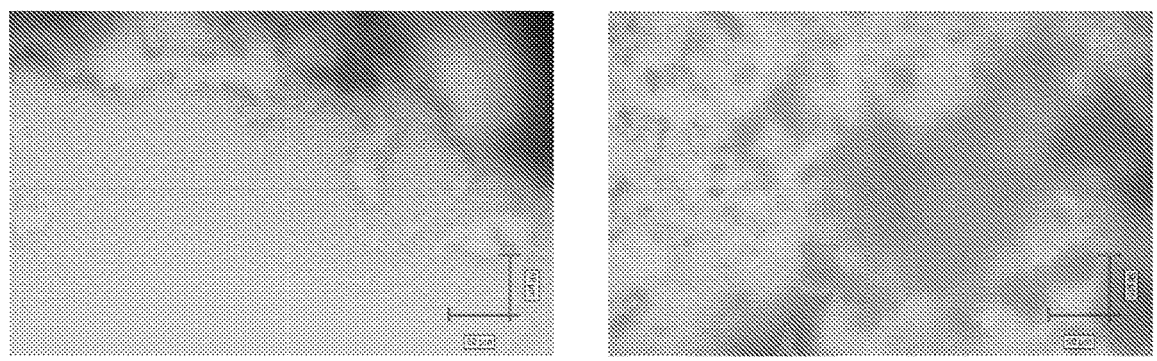
FIG. 23: confocal Raman microspectroscopy: simultaneous confocal laser scanning microscopy+Raman Spectroscopy in situ.

The chemical structure, crystal structures, and physical properties of sodium suramin alone are shown in FIGS. 1-8. Suramin alone is amorphous or liquid-crystalline (FIGS. 5-7) and is safe in a human cell line (FIG. 8).

In order to protect the drug in vivo, suramin was spray dried with trehalose using closed-mode nitrogen gas nanspray drying (See e.g., Mansour, H. M., et al., International Journal of Nanomedicine: (2009) 4 December: 299-319). A number of different variables were tested in a designed experiment in order to optimize spray drying parameters. The final parameters were: MeOH feed solvent, 0.5% w/v feed concentration, Tinlet set at 150° C., gas flow, aspirator rate, gas type is ultra-high purity (UHP) nitrogen gas (no water vapor and no oxygen present in UHP grade), pump rate/feed rate 25%. The feed composition was sodium suramin:trehalose at two molar ratios (20:80 and 50:50). Table 1 shows spray drying conditions used.

TABLE 1

| Spray Drying conditions | |
|---|---|
| Inlet Temperature | 150° C. |
| Aspirator rate | 100% |
| | 40 m³/hour |
| Pump Rate (PR) | 25% PR (7.5 ml/min) |
| Gas Flow | 670 L/hour |
| | 55 mm Hg |
| Feed Solution Concentration | 0.1% w/v |
| Solvent | Methanol |
| Atomizer and Drying gas | Ultra-High Purity (UHP) Nitrogen |
| Nozzle type diameter | Stainless steel 0.7 mm |

Results of suramin-trehalose at a 20:80 ratio are shown in FIGS. 9-12. Results show absence of characteristic sharp peaks (absence of long-range molecular order) indicative of a non-crystalline (amorphous) structure.

Results of surmain-trehalose at a 50:50 ratio are shown in FIGS. 13-16. Results show absence of characteristic sharp peaks (absence of long-range molecular order) indicative of a non-crystalline (amorphous) structure.

Example 2

This Example describes spray drying of suramin with PEGylated phospholipid particles.

DPPC (dipalmitoylphosphatidylcholine;

is a major constituent in biological membranes. It is a biocompatible and biodegradable-safety (FDA-approved excipient) currently used in currently marketed FDA-approved pharmaceutical products in oncology and infectious diseases. It exhibits encapsulation efficiency for hydrophobic drugs and is used as an immunomodulator of certain types of immune cells. DPPC has been shown to be biocompatible and biodegradable-safe in the lungs. Dipalmitoylphosphoethanolamine-poly(ethylene glycol)

(DPPE-PEG;

(2000 g/mol, 3000 g/mol, 5000 g/mol MW PEG used pharmaceutically) is FDA-approved in PEGylated nanomedicine products on the market. Only 5-10% PEG polymer concentration needed for appropriate surface coverage eliciting multifunctionality. PEG multi-functionality provides controlled drug release (e.g., sustained drug release over prolonged time) which lowers dosing frequency. DPPE-PEG is biocompatible, mucopenetrating, and can evade phagocytosis by immune cells (Meenach, S. A. Vogt, F. G., Anderson, K. W., Hilt, J. Z., McGarry, R. C., and Mansour, H. M. International Journal of Nanomedicine (2013) 8:275-293; Meenach, S. A. Anderson, K. W., Hilt, J. Z., McGarry, R. C., and Mansour, H. M. European Journal of Pharmaceutical Sciences (2013) 49 (4): 699-711).

Results of spray drying surmamin and a 95:5 ratio of DPPC:DPPE-PEG2000 at a 50:50 ratio are shown in FIGS. 16-23. Results shown particles are an amorphous gel bilayer.

Example 3

Figure 24:
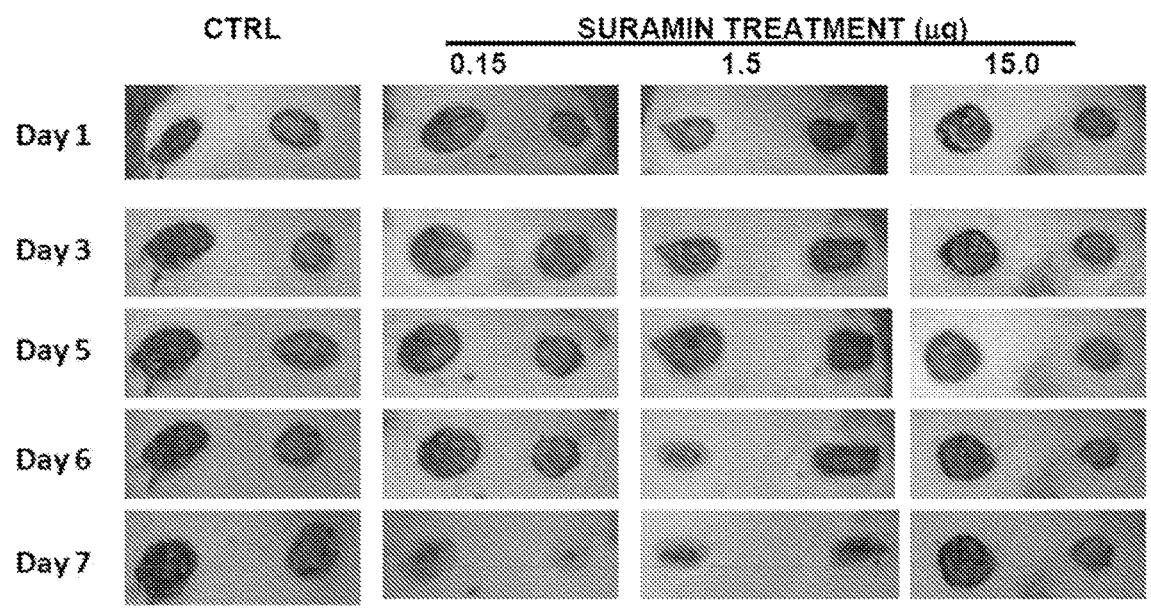
FIG. 24: suramin treatment results in accelerated wound healing in ob/ob mice.
Figure 25:
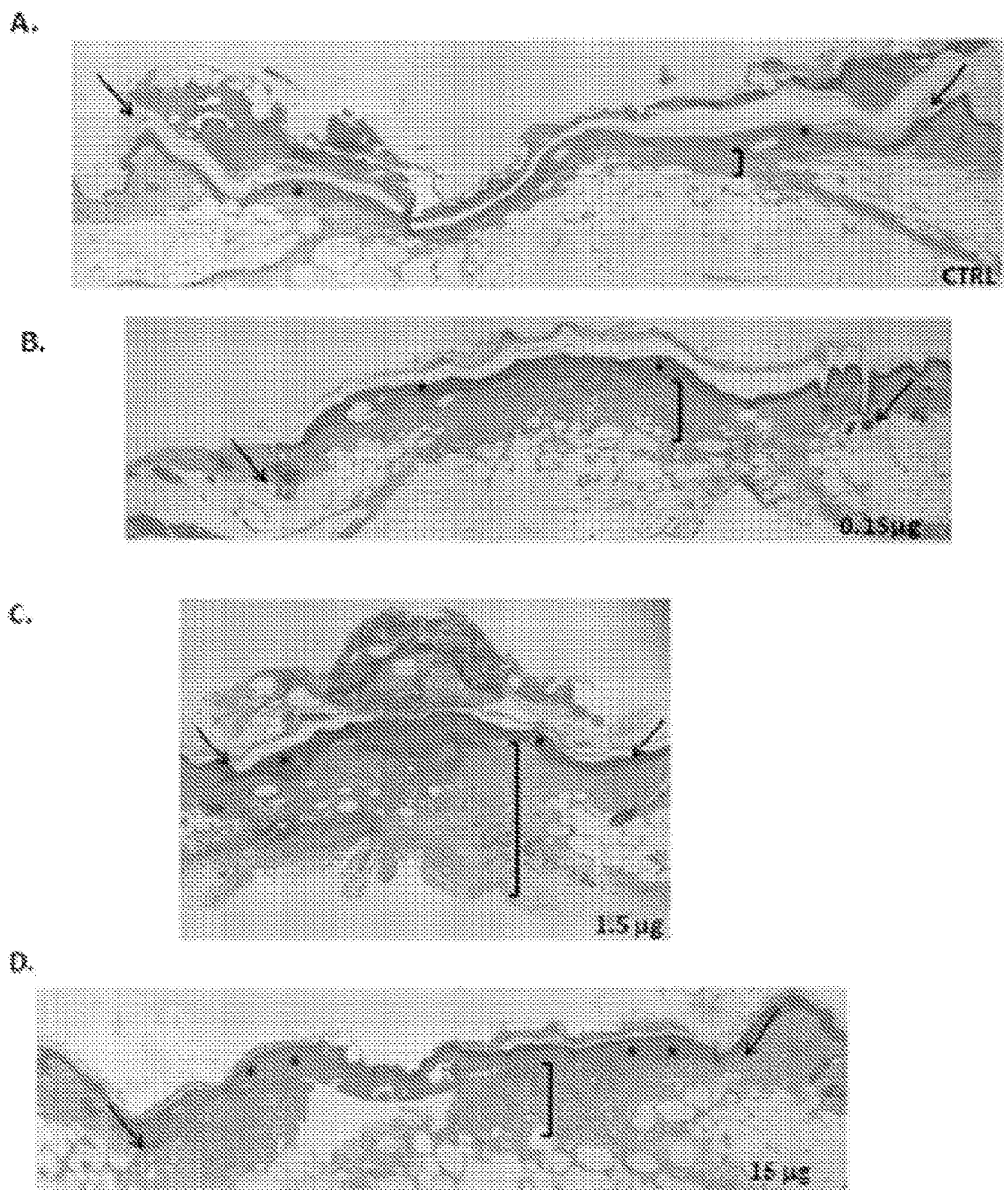
FIG. 25: suramin treatment results in increased granulation tissue and wound contraction. A) control. B) 0.15 µg surmain-treated; C) 1.5 µg surmain-treated; and d) 15 µg surmain-treated.

This Example describes accelerated wound healing in chronic wounds in diabetic and healthy mice. Results are shown in FIGS. 24 and 25. FIG. 24 shows that suramin treatment at different concentrations results in accelerated wound healing relative to controls. FIG. 25 shows that suramin treatment results in increased granulation tissue and wound contraction.

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

What is claimed is:

1. A composition, comprising: suramin nanoparticles or microparticles and a pharmaceutically acceptable carrier, wherein said pharmaceutically acceptable carrier is selected from the group consisting of a) trehalose and b) a mixture of dipalmitoylphosphatidylcholine (DPPC) and dipalmitoylphosphoethanolamine-poly(ethylene glycol) (DPPE-PEG).

2. The composition of claim 1, wherein said suramin and trehalose are present at a molar ratio of 20:80 to 80:20.

3. The composition of claim 1, wherein said suramin and trehalose are present at a molar ratio of 50:50.

4. The composition of claim 1, wherein said suramin and said mixture of DPPC and DPPE-PEG are present at a molar ratio of 50:50.

5. The composition of claim 1, wherein said suramin is encapsulated by said mixture of DPPC and DPPE-PEG.

6. The composition of claim 1, wherein said DPPC and DPPE-PEG are present at a 95:5 molar ratio.

7. The composition of claim 1, wherein said PEG has an average molecular weight of 2000 g/mol to 5000 g/mol.

8. The composition of claim 1, wherein said composition is prepared by spray drying.

9. The composition of claim 1, wherein said nanoparticles or microparticles are amorphous.

10. The composition of claim 1, wherein said nanoparticles or microparticles are generated by a method, comprising:

a) preparing a first solution comprising said suramin in an organic solvent and a second solution comprising said pharmaceutically acceptable carrier in said organic solvent; and b) co-spraying said first and second solutions using a spray drying apparatus to generate said nanoparticles or microparticles.

11. The composition of claim 10, wherein said organic solvent is methanol.

12. A method of treating wounds in a subject of need thereof, the method comprising topically administering the composition of claim 1 to the wound of the subject.

13. The method of claim 12, wherein said wound is selected from the group consisting of an acute wound, a chronic wound and ulcer.

14. The method of claim 12, wherein said subject has diabetes or mucositis.

15. The method of claim 12, further comprising administering an additional treatment for said wound.

* * * * *